United States Patent [19]

Marko et al.

[11] 4,363,809

[45] Dec. 14, 1982

[54] ORGANIC COMPOUNDS

[75] Inventors: Magda Marko, Binningen, Switzerland; Hendricus B. A. Welle, Maarssen, Netherlands

[73] Assignee: Sandoz Ltd., Basel, Switzerland

[21] Appl. No.: 282,813

[22] Filed: Jul. 13, 1981

Related U.S. Application Data

[63] Continuation-in-part of Ser. No. 173,306, Jul. 29, 1980, abandoned.

[30] Foreign Application Priority Data

Aug. 3, 1979 [GB] United Kingdom ............... 7927061

[51] Int. Cl.³ ........................................ A61K 31/485
[52] U.S. Cl. ...................................... 424/260; 546/97
[58] Field of Search ........................... 424/260; 546/97

[56] References Cited

U.S. PATENT DOCUMENTS

| | | | |
|---|---|---|---|
| 3,320,265 | 5/1967 | Clarke | 546/97 |
| 3,513,169 | 5/1970 | Robinson et al. | 546/97 |
| 4,010,164 | 3/1977 | Langbein et al. | 546/97 |
| 4,012,392 | 3/1977 | Akkerman et al. | 546/97 X |
| 4,020,164 | 4/1977 | Rahtz et al. | 546/97 X |

OTHER PUBLICATIONS

Tataryn et al., "4 Int'l. Symposium on the Pharmacology of Thermoregulation", publ. by Karger, Basel, (1980), pp. 202–207.
Casper et al., Science, 205, pp. 823–825, (1979).

*Primary Examiner*—Stanley J. Friedman
*Attorney, Agent, or Firm*—Gerald D. Sharkin; Robert S. Honor; Thomas O. McGovern

[57] ABSTRACT

Method of inhibiting luteinising hormone secretion in a subject, said method comprising administering an optionally 5-alkyl- or -phenyl- and/or 2'-hydroxy-, -alkoxy- or -acyloxy-substituted 9,9-dimethyl-6,7-benzomorphan derivative having an oxygen containing substituent at the N-atom.

10 Claims, No Drawings

ORGANIC COMPOUNDS

The present application is a continuation-in-part of our previous application Ser. No. 173,306 filed July 29, 1980, now abandoned.

The present invention relates to a new use for the compounds of formula I:

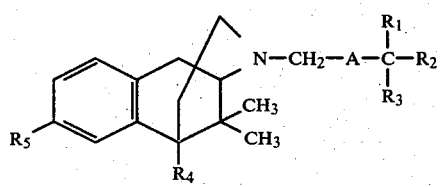

wherein

A is a direct bond or —CH₂—,

R₁ is hydrogen, $C_{1-3}$alkyl, $C_{2-3}$alkenyl, $C_{2-3}$alkynyl, $C_{1-2}$alkoxy, $C_{1-2}$alkyl or $C_{3-6}$cycloalkyl, R₂ is hydrogen or $C_{1-3}$alkyl, or R₁ and R₂, together with the carbon atom to which they are attached, form a $C_{3-6}$cycloalkyl group or a 4 to 6-membered heterocycloalkyl group containing one oxygen atom as the sole hetero atom, R₃ is hydroxy, $C_{1-4}$alkoxy, $C_{2-4}$alkenyloxy, or R₆COO— in which R₆ is hydrogen, $C_{1-3}$alkyl, phenyl or benzyl, R₄ is hydrogen, $C_{1-4}$alkyl or phenyl, and R₅ is hydrogen, hydroxy, $C_{1-3}$alkoxy or R₇COO— where R₇ is hydrogen, $C_{1-3}$alkyl, phenyl, benzyl, phenethyl or 3-pyridyl.

The compounds of the formula I as well as processes for their production are known e.g. from European Patent Application No. 79101161.2 (Publication No. 4960) filed Apr. 17, 1979 and corresponding applications in the United States (application Ser. No. 31780, filed Apr. 20, 1979) Japan (application No. 51981/79, filed Apr. 26, 1979), Italy (application No. 48786A/79, filed Apr. 19, 1979) and New Zealand (application No. 190278, filed Apr. 24, 1979), the contents of which are incorporated herein by reference.

The compounds are described as having analgesic and/or morphine antagonistic activity.

In accordance with the present invention it has now surprisingly been found that the compounds of formula I are also useful in that they inhibit luteinising hormone secretion as shown by standard animal tests such as hereinafter described.

In view of their LH-secretion inhibiting activity, compounds of formula I are useful in the treatment of disorders having an aetiology associated with or modulated by LH-secretion or having an aetiology in which the physiological regulation of LH-secretion is implicated e.g. in the treatment of prostate hypertrophy or in the treatment of menopausal syndrome, in particular post-menopausal hot flashes e.g. in accordance with the studies reported by Tataryn et al. ["Thermoregulatory Mechanisms and their Therapeutic Implications, 4th. Int. Symp. on the Pharmacology of Thermoregulation, Oxford, 1979" published by Karger, Basel 1980, pp. 202–207] and Casper et al. ["Science", 205, pp. 823–825 (1979)].

In accordance with the foregoing the present invention provides a method of inhibiting luteinising hormone secretion, in particular a method of treating prostatic hypertrophy or menopausal syndrome, especially post-menopausal hot flashes, in a subject in need of such treatment, which method comprises administering to said subject an effective amount of a compound of formula I as hereinbefore defined.

Of the compounds specifically recited in the aforementioned patent applications the following are preferred for use in accordance with the present invention:

A. 9,9-Dimethyl-5-ethyl-2'-hydroxy-2-(1-hydroxycyclopropylmethyl)-6,7-benzomorphan [Bremazocine, also known as 6-ethyl-1,2,3,4,5,6-hexahydro-3-(1-hydroxycyclopropylmethyl)-11,11-dimethyl-2,6-methano-3-benzazolin-8-ol];

B. 9.9-Dimethyl-2'-hydroxy-2-(1-hydroxycyclopropylmethyl)-5-n-propyl-6,7-benzomorphan [also known as 1,2,3,4,5,6-hexahydro-3-(1-hydroxycyclopropylmethyl)-11,11-dimethyl-6-n-propyl-2,6-methano-3-benzazocin-8-ol];

C. 9,9-Dimethyl-2'-hydroxy-2-(1-hydroxycyclopropylmethyl)-5-methyl-6,7-benzomorphan [also known as 1,2,3,4,5,6-hexahydro-3-(1-hydroxycyclopropylmethyl)-6,11,11-trimethyl-2,6-methano-3-benzazocin-8-ol]; and D. 9,9-Dimethyl-2'-hydroxy-2-(1-hydroxycyclopropylmethyl)-5-phenyl-6,7-benzomorphan [also known as 1,2,3,4,5,6-hexahydro-3-(1-hydroxycyclopropylmethyl)-11,11-dimethyl-6-phenyl-2,6-methano-3-benzazocin-8-ol].

In accordance with the invention the compounds of formula I may be administered in free base form or in pharmaceutically acceptable acid addition salt form. Such acid addition salt forms are also known and include the hydrochloride and oxalate.

The activity of such pharmaceutically acceptable salt forms will generally be of the same order as that of the respective free base form. As used herein all amounts of such compounds recited refer to the amount of the free base form unless otherwise indicated. The same applies to weight ratios.

Equally the compounds of formula I may be used in racemic form or in the form of individual optical antipodes. While individual antipodes may exhibit a higher order of activity, for ease of preparation use of the racemate is generally preferred.

The luteinising hormone secretion inhibiting activity of the compounds of formula I, e.g. compound A or B as set forth hereinabove, may be demonstrated in animal tests, e.g. by an inhibition of ovulation or by direct assay of luteinising hormone levels in the blood serum, for example in accordance with the following methods:

Adult female rats of the Ivanovas Wistar strain each weighing 200–250 g were maintained under standard conditions [14 hours light (04.00–18.00 h), 24° C. and 55–60% relative humidity] and allowed access ad libitum to food and water. Animals with a proven, regular 4-day oestrus cycle received the test compound either subcutaneously or orally during the pro-oestrus phase, the doses being administered once at 13.00 h and again at 16.00 h. 20 Hours after the first dose, the rats were sacrificed, the fallopian tubes exposed and the total number of ova in both tubes counted with a disecting microscope. Ovulation was considered to have been inhibited only when no ova were found.

Five rats were used per dose and 6 or 7 doses each for the subcutaneous and oral routes of administration were studied. The ED₅₀, estimated according to the method described by Litchfield and Wilcoxon [J. Pharm. Exp. Ther. 96, 99 (1949)], was taken as the dose that inhibited ovulation from occurring in 50% of rats compared with the results obtained using untreated controls.

In general the test compounds were found to be effective in a range of from about 2×0.0005 to 1 mg/kg and from about 2×0.05 to 2×3.0 mg/kg for the subcutaneous and oral routes of administration respectively.

In accordance with a second test method adult, female golden hamsters (Mesocricetus auratus, Füllinsdorf) weighing ca. 100 g were maintained under standard conditions exactly as hereinabove described and allowed access ad libitum to food and water. Animals with a regular, proven 4-day oestrus cycle received the test compound subcutaneously in three doses during the prooestrus phase at 11.00, 13.00 and 16.00 h. 22 Hours after the first injection when the hamsters were in oestrus, the animals were sacrificed, the fallopian tubes exposed and the total number of ova in both tubes counted. Again ovulation was considered to have been inhibited only when no ova were found and the $ED_{50}$ was estimated as in the previously described test method.

In this test the compounds were in general found to be effective in a range of from about 3×0.005 to 3×0.3 mg/kg s.c.

A third test method involves direct assay of luteinising hormone levels in the blood serum. For this test female rats of the Ivanovas Wistar strain were ovariectomised under Evipan anaesthesia. Twenty days after recovery, the test compound was administered subcutaneously at varying dosages. One hour after administration, the rats were decapitated and the serum luteinising hormone levels determined using standard radioimmunoassay technique. Five rats were used per dose and the mean level of luteinising hormone found in the animals expressed as a percentage of the mean level obtained in solvent-treated controls.

In this test compounds of formula I were generally found to be effective in a range of from about 0.01 to 10 mg/kg.

The amount of compound administered in practising the method of the invention will of course vary according to e.g. the particular compound employed, the mode of administration, the condition to be treated and the therapy desired.

In general satisfactory results are obtained depending on the mode of administration, e.g. s.c. or oral, with a daily dosage of from about 0.001 to about 1.0 mg/kg. Conveniently the compound is presented in unit dosage form administered 2 to 4 times a day or in sustained release form.

For the larger mammal a suitable oral daily dosage is from about 0.1, preferably about 0.5 mg, to about 20, preferably about 4.0 mg, suitably administered in unit dosage form containing about 0.025, preferably about 0.125, to about 10, preferably about 2 mg, of the compound of formula I.

Pharmaceutical compositions for use in the method of the invention may be prepared in accordance with standard techniques for example by admixture of the compound of formula I with conventional pharmaceutically acceptable diluents or carriers and optionally other excipients. Suitable forms for administration include tablets, capsules and injectable solutions. Solid forms suitable for oral administration are preferred.

In addition to the foregoing the present invention also provides a pack containing a pharmaceutical composition comprising a compound of formula I as hereinabove defined, together with instructions for the administration of said composition as a means of inhibiting luteinising hormone secretion and in particular with instructions for the administration of said composition in the treatment of prostatic hypertrophy or menopausal syndrome.

The following examples illustrate compositions useful in the treatment of prostate hypertrophy and menopausal syndrome.

EXAMPLE 1

Production of solid pharmaceutical compositions

Tablets may contain the active agent in admixture with conventional pharmaceutically acceptable excipients, e.g. inert diluents, such as calcium carbonate, sodium carbonate and lactose, granulating and disintegrating agents, e.g. starch and alginic acid, flavouring, colouring and sweetening agents, binding agents, e.g. starch, gelatin and acacia, and lubricating agents, e.g. magnesium stearate, stearic acid and talc. The tablets may be coated by known techniques to delay disintegration and absorption in the gastrointestinal tract and thereby provide a sustained action over a long period.

For the manufacture of tablets, the compounds of formula I can be mixed with lactose and granulated with water, 0.5% sodium alginate or 1% gelatine solution. The dried granulate is compressed into tablets in the presence of about 5% of silica, 5% of corn starch and 0.1% of magnesium stearate. In this way, there are obtained, e.g. tablets of the following compositions:

| Ingredient | Weight (mg) |
|---|---|
| Compound of formula I, e.g. compound A hereinabove referred to, in the form of its hydrochloride | 1.116 (= 1 mg base) |
| Lactose | 27.7 |
| Corn Starch | 15.0 |
| Colloidal silica (Aerosil 200) | 2.5 |
| Magnesium stearate | 0.9 |

These tablets, which are provided with a crackline, can be administered orally in a dosage of one tablet two to four times per day.

Capsules may contain the active agent alone or admixed with an inert solid diluent, for example as mentioned above. A suitable formulation for filling into capsules is as follows:

| Ingredient | Weight (mg) |
|---|---|
| Compound of formula I, e.g. compound A hereinabove referred to, in the form of its hydrochloride | 1.116 (= 1 mg base) |
| Cornstarch | 100.0 |
| Powdered tartaric acid | 1.0 |
| Lactose (100 mesh) | 150.0 |
| Lactose (200 mesh) | 240.384 |
| Magnesium stearate | 5.0 |
| Colloidal silica (Aerosil 200) | 2.5 |

The above ingredients are formulated and filled into capsules in accordance with conventional techniques. The capsules are administered at a dose of one capsule 2 to 4 times a day.

5 and 20 mg capsules may be prepared using the following formulations:

| | Ingredient | Weight (mg) |
|---|---|---|
| (i) | Compound A as HCl salt | 22.32 (= 20 mg base) |
| | Corn starch | 100.00 |
| | Tartaric acid (powdered) | 1.00 |
| | Lactose (100 mesh) | 150.00 |
| | Lactose (200 mesh) | 219.18 |
| | Magnesium stearate | 5.00 |
| | Colloidal silica (Aerosil 200) | 2.50 |
| | Total | 500.00 |

| | Ingredient | Weight (mg) |
|---|---|---|
| (ii) | Compound A as HCl salt | 5.58 (= 1 mg base) |
| | Corn starch | 100.00 |
| | Tartaric acid (powdered) | 1.00 |
| | Lactose (100 mesh) | 150.00 |
| | Lactose (200 mesh) | 235.92 |
| | Magnesium stearate | 5.00 |
| | Colloidal silica (Aerosil 200) | 2.50 |
| | Total | 500.00 |

The compositions are compounded and filled into capsules in accordance with standard techniques.

EXAMPLE 2

Production of liquid pharmaceutical compositions

Solutions and suspensions suitable for injection may contain the compound of formula I as the above agent in the form as described in the proceeding example in admixture with any of the conventional excipients utilized for the preparation of such compositions, e.g. utilized for the preparation of such compositions, e.g. suspending agents (methylcellulose, tragacanth and sodium alginate), wetting agents (lecithin, polyoxyethylene stearate and polyoxyethylene sorbitan monoleate) and preservatives (ethyl-p-hydroxybenzoate.

The following ingredients, suitable for a sterile injectable suspension, are formulated with the indicated amount of active agent using conventional techniques and is suitable for administration once a day.

| Ingredient | Weight (mg) |
|---|---|
| Compound of formula I, e.g. as an acid addition salt | 0.02 |
| Sodium carboxy methyl cellulose U.S.P. | 1.25 |
| Methyl cellulose | 0.4 |
| Polyvinylpyrrolidone | 5 |
| Lecithin | 3 |
| Benzyl alcohol | 0.01 |
| Buffer agent to adjust pH for desired stability | q.s. |
| Water | q.s. to 1 ml. |

What we claim is:

1. A method of inhibiting luteinizing hormone secretion in a subject in need of such treatment, which method comprises administering to said subject a luteinizing hormone inhibiting effective amount of a compound of formula I,

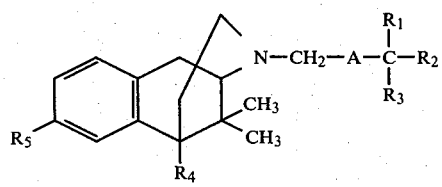

wherein
A is a direct bond or —CH$_2$—,
R$_1$ is hydrogen, C$_{1-3}$alkyl, C$_{2-3}$alkenyl, C$_{2-3}$alkynyl, C$_{1-2}$alkoxy, C$_{1-2}$alkyl or C$_{3-6}$cycloalkyl,
R$_2$ is hydrogen or C$_{1-3}$alkyl, or
R$_1$ and R$_2$, together with the carbon atom to which they are attached, form a C$_{3-6}$-cycloalkyl group or a 4 to 6-membered heterocycloalkyl group containing one oxygen atom as the solo hetero atom,
R$_3$ is hydroxy, C$_{1-4}$alkoxy, C$_{2-4}$alkenyloxy, or R$_6$COO— in which R$_6$ is hydrogen, C$_{1-3}$-alkyl, phenyl or benzyl,
R$_4$ is hydrogen, C$_{1-4}$alkyl or phenyl, and
R$_5$ is hydrogen, hydroxy, C$_{1-3}$alkoxy or R$_7$COO— where R$_7$ is hydrogen, C$_{1-3}$alkyl, phenyl, benzyl, phenethyl or 3-pyridyl.

2. A method according to claim 1, wherein the compound of formula I is 9,9-dimethyl-5-ethyl-2'-hydroxy-2-(1-hydroxycyclopropylmethyl)-6,7-benzomorphan.

3. A method according to claim 1, wherein the compound of formula I is 9,9-dimethyl-2'-hydroxy-2-(1-hydroxycyclopropylmethyl)-5-n-propyl-6,7-benzomorphan.

4. A method according to claim 1, wherein the compound of formula I is 9,9-dimethyl-2'-hydroxy-2-(1-hydroxycyclopropylmethyl)-5-methyl-6,7-benzomorphan.

5. A method according to claim 1, wherein the compound of formula I is 9,9-dimethyl-2'-hydroxy-2-(1-hydroxycyclopropylmethyl)-5-phenyl-6,7-benzomorphan.

6. A method according to claim 1 for the treatment of menopausal syndrome.

7. A method according to claim 6 for the treatment of post-menopausal hot flashes.

8. A method according to claim 1 for the treatment of prostatic hypertrophy.

9. A method according to claim 1, wherein the compound is administered at a daily dosage of from about 0.1 to about 20 mg.

10. A method according to claim 9, wherein the compound is administered at a daily dosage of from about 0.5 to about 4 mg.

* * * * *